US00PP13678P39

(12) United States Plant Patent
Datta

(10) Patent No.: US PP13,678 P3
(45) Date of Patent: Mar. 25, 2003

(54) CHRYSANTHEMUM PLANT NAMED 'MOTHER TERESA'

(75) Inventor: Subodh Kumar Datta, Lucknow (IN)

(73) Assignee: Council of Scientific and Industrial Research, New Delhi, IN (US)

( * ) Notice: Subject to any disclaimer, the term of this patent is extended or adjusted under 35 U.S.C. 154(b) by 5 days.

(21) Appl. No.: 09/821,100

(22) Filed: Mar. 30, 2001

(65) Prior Publication Data

US 2002/0178476 P1 Nov. 28, 2002

(51) Int. Cl.[7] ..... A01H 5/00

(52) U.S. Cl. ..... Plt./294

(58) Field of Search ..... Plt./294

*Primary Examiner*—Bruce R. Campell
*Assistant Examiner*—A Para
(74) *Attorney, Agent, or Firm*—Foley & Lardner

(57) ABSTRACT

The present invention relates to a novel hybrid plant of *Chrysanthemum morifolium* Ramat christened as 'Mother Teresa' and having dwarf, bushy, compact round shaped., profuse blooming habit, producing white Anemone type flowers with distinct white ray florets and creamish white disc florets, green foliage with few white streaks and requiring neither 'Pinching' nor 'Staking'.

1 Drawing Sheet

LATIN NAME OF THE GENUS AND SPECIES OF THE PLANT CLAIMED

*Chrysanthemum morifolium* Ramat.

VARIETY DENOMINATION

Mother Teresa.

FIELD OF THE INVENTION

The present invention relates to a new ornamental chrysanthemum plant christened as 'Mother Teresa'.

BACKGROUND OF THE INVENTION

The present invention relates to a new and distinct variety of *Chrysanthemum morifolium* Ramat, a member of the Chrysanthemum genus, which has been developed using the open pollinated seedling method. *Chrysanthemum morifolium* is a popular flower crop of world-wide commercial importance. Chrysanthemum varieties have earned tremendous popularity as an ornamental flower for garden, as cut flowers for interior decoration and loose flower. Demand of new and novel varieties of Chrysanthemum are increasing day-by-day in the world floriculture trade.

Chrysanthemum can be propagated both by seed and vegetative means. Cross breeding and selective breeding helped in developing large number of new varieties. The genotype 'Mother Teresa' has evolved through seedling selections of open pollinations among specific group of chrysanthemum. The new genotype evolved in this invention represents such an improvement combining novel flower colour and shape and plant stature. The new variety offers the floriculturists/nurserymen an improved attractive novel ornamental plant which can be commercially cultivated.

SUMMARY OF THE INVENTION

The present invention provides a new arid distinct hybrid *Chrysanthemum morifolium* variety christened as 'Mother Teresa' characterized by profuse blooming habit, dwarf bush, white Anemone type mini plant habit.

DETAILED DESCRIPTION OF THE INVENTION

The invention provides a new, novel and distinct hybrid *Chrysanthemum morifolium* plant christened as 'Mother Teresa', having the following combination of characters:

(a) Green foliage with few white streaks, (b) White Anemone type flower;

(c) Dwarf bushy, compact round shaped, profuse blooming plant, suitable for mini culture;

(d) Pigment composition of petals being distinct from other existing varieties, and (f) True-to-type performance under different environments.

The new variety of this invention is a *Chrysanthemum morifolium* genotype, christened as 'Mother Teresa'. This plant has been developed through planned breeding programmes conducted at National Botanical Research Institute, Lucknow, India with an aim to develop a new hybrid variety of *Chrysanthemum morifolium.* For this purpose existing mini varieties of chrysanthemum i.e. Haldighati and Swarna Singar (unpatented varieties) were grown very closely in the field in August 1989 at Lucknow, India facilitating pollination among themselves. The seeds borne on existing cultivars (Haldighati and Swarna Singar) were collected in January 1990 and were sown in February 1990. One of the plants in the field was a dwarf plant that exhibited Anemone type flowers and profuse blooming. This plant was given number DWS 13 and was selected for further observation and evaluation.

Considering the attractive flower colour and shape and plant growth habit, it was asexually reproduced in Lucknow, India through suckers to maintain clonal purity. The selected clone DWS 13 was grown both in beds and 10" earthen pots alongwith existing mini varieties (Haldighati and Swarna Singar) for five successive generations from 1990 upto 1995. The clone DWS 13 maintained its flower colour and shape and plant growth habit in all the generations. This plant was found to be different from all other chrysanthemum plants in colour of flowers, shape and pigment composition of petals.

In the subsequent year (1996), the genotype DWS 13 was evaluated in both replicated field and pot trial alongwith existing parents to study the flower colour and shape and plant growth habit. The clone DWS 12 bred true to type and proved very attractive over the existing varieties in quality of bloom including colour, shape and type of bloom. Chrysanthemum cultivation (large and small flowered cultivars) require lot of cultural operations including 'Pinching' and 'Staking'. For small flowered Chrysanthemum apical shoot tips are cut (half to one inch) to give proper shape to the plant. This operation is called "Pinching" and "Staking" is necessary to keep plants erect and to maintain proper shape of plant and bloom. These operations are expensive and time consuming.

National Botanical Research Institute, Lucknow, India has already developed 'Mini Chrysanthemum' which is unique of its kind. It requires neither 'Pinching' nor 'Staking'. It is a unique genetic strain with dwarf; bushy, compact round shaped, profuse blooming habit. Number of existing mini varieties and their colour is very limited at present. Efforts were made to develop new flower colour under an on going improvement research programme.

The new clone DWS 13, selected from open pollinated, seedling, is a product of this Research Programme and has been Christened 'Mother Teresa'.

EVIDENCE OF UNIFORMITY AND STABILITY

The genotype 'Mother Teresa' has remained stable and uniform for its morphological characters and showed consistency in performance for various vegetative and floral quality attributes during its evaluation and vegetative multiplication from 1990 until 1995.

No variation was detected in morphological characters especially in the flower colour characters through vegetative multiplication during large scale propagation, testing and field trial upto 1997.

BRIEF DESCRIPTION OF THE DRAWING

The accompanying photographic drawing shows the typical flower characteristics of 'Mother Theresa' with colors as true as possible with an illustration of this type. The photographic drawing depicts a pot grown plant of 'Mother Teresa' showing the flower arrangement, shape, and colour.

STATEMENT OF DISTINCTION

The genotype 'Mother Teresa' possesses small, thin green leaves with very small white streaks on it, white Anemone type flower, dwarf, bushy, compact round shaped, profuse blooming habit.

The genotype 'Mother Teresa' is distinct in regeneration potential in second and subsequent generations in morphological and flower characters.

Repeated petal extracts from different plants of Mother Teresa showed the same peaks for pigments in spectrophotometer.

PIGMENT ANALYSIS

The main difference between new hybrid 'Mother Teresa' and two existing parental varieties (Haldighati and Swarna Singar) was in flower colour and shape. Therefore, flower pigment of three genotypes were analyzed to establish the relatedness among them.

For detection of pigment composition florets (1 gm) of three genotypes were extracted in methanol containing 1% HCl and centrifuged. The supernatant was taken into volumetric flask and volume was made upto 50 ml. The extract was scanned from 200 to 700 nm wavelength in spectrophotometer. The details of compound in different genotypes are as follows:

| Genotype | No. of Peak (Compound) | Peak Height | Wave length |
|---|---|---|---|
| Mother Teresa | 1 | 0.768 | 204.3 |
| | 2 | 0.256 | 268.2 |
| Haldighati | 1 | 0.450 | 192.1 |
| | 2 | 1.419 | 204.5 |
| | 3 | 0.887 | 328.0 |
| | 4 | 0.093 | 415.4 |
| | 5 | 0.122 | 434.8 |
| | 6 | 0.109 | 462.0 |
| Swarna Singar | 1 | 0.609 | 193.1 |
| | 2 | 2.079 | 206.6 |
| | 3 | 0.882 | 248.6 |
| | 4 | 0.780 | 268.1 |
| | 5 | 0.177 | 330.4 |
| | 6 | 0.192 | 434.3 |
| | 7 | 0.167 | 462.1 |

Pigment analysis clearly indicate that genotype 'Mother Teresa' was very distinct in pigment composition from two other parental genotypes both qualitatively and quantitatively.

Ojective Description of the Variety "Mother Teresa" (DWS 13)

The following is an objective description of a 5 month old plant of 'Mother Teresa':

Genus: Chrysanthemum.
Species: *morifolium* Ramat.
Family: Compositae.
Common name: English: Chrysanthemum; Local names: Sanskrit — Sevanti; Hindi — Guldaudi; Bengali — Chandramallika; Marathi — Shevati; Tamil — Akkarakkaram; Telgu — Chamunti; Punjabi — Gondi, Bagaura; Urdu — Guledawoodi.
Plant height: About 22 cm.
Growth habit: Dwarf, busy, compact.
Blooming period: December–January, responds to short or long day treatment; blooming period may be prompted or delayed by photoperiodic treatment.
Time it takes to produce a rooted cutting: Approximately 15 days under Lucknow, India conditions in July.
Cold tolerance: To 5° C.
Stem: Quadrangular, green RHS 138C.
Lateral branches: Mostly alternate with profuse short length terminal branches.
Leaf: Small, thin, green with very small white streaks.
*Texture.*—Thin.
*Surface.*—Smooth (rarely few hairs).
*Shape.*—Oval.
*Margin.*—Serrated.
*Tip.*—Acute.
*Size.*—Broad.
*Length.*—3.2 cm.
*Width.*—1.8 cm.

*Color.*—Upper surface green RHS 137A. Lower surface green RHS 138B.

*Petiole length.*—0.4 cm.

Inflorescence: Capitullum.

*Ray florets.*—White, 1–2 whorl.

*Disc florets.*—Compact, slightly creamish white, disc very prominent, 180–210 disc florets per head, apex rounded, 0.8–1.2 cm in length.

Flower type: Anemone.

Peduncle: Short, 3–4 cm in length, smooth surface, green RHS 138D.

Seeds: Low production, size: smaller than 1 mm, dark grey in color.

The salient features of 'Mother Teresa' and two other existing varieties are as follows.

| | Varieties | | |
|---|---|---|---|
| Characters | Mother Teresa | Haldighati | Swrana Singar |
| Leaf length (cm) | 3.2 | 2.6 | 2.4 |
| Leaf width (cm) | 1.8 | 1.4 | 1.5 |
| Petiole length (cm) | 0.4 | 1.1 | 1.0 |
| Plant height (cm) | 22 | 27.5 | 14.0 |
| Floret/head | 34 | 32 | 76 |
| Floret length (cm) | 1.2 | 1.2 | 1.3 |

-continued

| | Varieties | | |
|---|---|---|---|
| Characters | Mother Teresa | Haldighati | Swrana Singar |
| Floret width (cm) | 0.5 | 0.4 | 1.4 |
| Bloom type | 1–2 whorl ray floret, flat, disc prominent, Anemone type | 1–3 whorl ray floret, flat, disc prominent, Decorative type | Double Korean |
| Floret colour | White ray floret, light yellowish White group (158A) FAN 4 | Bright yellow Yellow group (9A) FAN 1 | Yellow group (12A) FAN 1 |
| No. of pigment | 2 | 6 | 7 |

The floret colour which is the main novelty of ornamentals was identified in the present varieties according to R.H.S. Colour Chart published by The Royal Horticultural Society, London in association with the Flower Council of Holland, 1966.

I claim:

1. A new and distinct plant of *Chrysanthemum morifolium* Ramat christened as 'Mother Teresa' as herein described and shown.

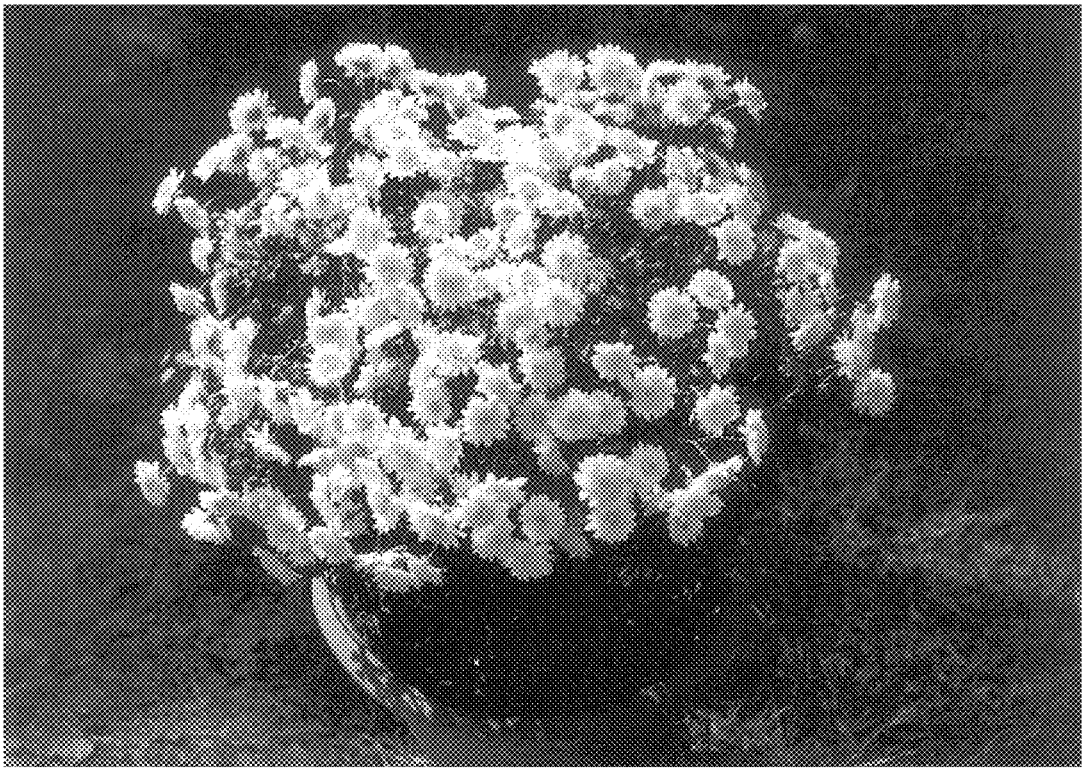

* * * * *